United States Patent [19]

Badorc et al.

[11] Patent Number: 4,740,510
[45] Date of Patent: Apr. 26, 1988

[54] DERIVATIVES OF ALPHA-(2-OXO 2,4,5,6,7,7A-HEXAHYDRO THIENO[3,2-C]5-PYRIDYL) PHENYL ACETIC ACID, AND THEIR USE AS PLATELET AND THROMBOTIC AGGREGATION INHIBITORS

[75] Inventors: Alain Badorc, Roquettes; Daniel Frehel, Toulouse; Jean-Pierre Maffrand, Portet/Garonne; Eric Vallee, Tournefeuille, all of France

[73] Assignee: Sanofi (S.A.), Paris, France

[21] Appl. No.: 825,068

[22] Filed: Jan. 31, 1986

[30] Foreign Application Priority Data

Jan. 31, 1985 [FR] France ................. 8501908

[51] Int. Cl.[4] .................. A61K 31/435; C07D 471/04
[52] U.S. Cl. ..................... 514/291; 546/114; 544/127; 514/227; 514/238; 514/240
[58] Field of Search ................. 546/114; 544/127

[56] References Cited

U.S. PATENT DOCUMENTS 4,424,356  1/1984  Maffrand et al. ............... 546/114

Primary Examiner—Henry R. Jiles
Assistant Examiner—J. Richter
Attorney, Agent, or Firm—Wegner & Bretschneider

[57] ABSTRACT

The present invention relates to novel derivatives of alpha-(2-oxo 2,4,5,6,7,7a-hexahydro thieno [3,2-c] 5-pyridyl) phenyl acetic acid corresponding to the following general formula:

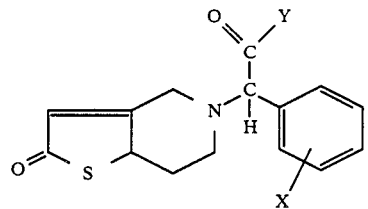

their addition salts with pharmaceutically-acceptable inorganic or organic acids as well as isomers and their mixtures.

The invention also relates to their process of preparation and to medicaments containing these compounds which are of therapeutic use as inhibitors of platelet- and thrombotic-aggregation.

16 Claims, No Drawings

DERIVATIVES OF ALPHA-(2-OXO 2,4,5,6,7,7A-HEXAHYDRO THIENO[3,2-C]5-PYRIDYL) PHENYL ACETIC ACID, AND THEIR USE AS PLATELET AND THROMBOTIC AGGREGATION INHIBITORS

This application claims priority to French patent application Ser. No. 8,501,908 filed on Jan. 31, 1985.

The invention relates to novel derivatives of alpha-(2-oxo 2,4,5,6,7 7a-hexahydro thieno [3,2-c]5-pyridyl) phenyl acetic acid, to a process for preparing them, and to their therapeutic uses.

These derivatives correspond to the following general formula:

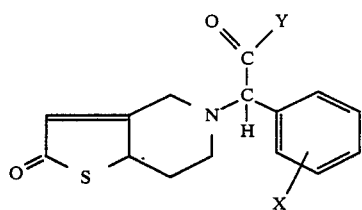

in which Y represents hydroxyl (—OH); or Y represents the group (—OR) in which R is a linear or branched lower alkyl radical, or an aralkyl radical optionally substituted on the phenyl nucleus, or a dialkyl-aminoalkyl group of the formula:

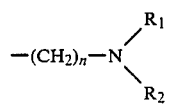

in which n represents a whole number from 1 to 4, $R_1$ and $R_2$ are each a lower alkyl radical or $R_1$ and $R_2$ form together and with the nitrogen atom to which they are attached, a heterocyclic ring which can include a second heteroatom such as oxygen, sulfur or nitrogen, the latter being optionally substituted by a lower alkyl radical; or Y represents an amino group of the formula:

in which $R_3$ and $R_4$, which can be the same or different, are each hydrogen or a linear or branched lower alkyl group, saturated or unsaturated, an aryl or aralkyl group optionally substituted, a heteroaryl or heteroaralkyl group, or $R_3$ and $R_4$ form together with the nitrogen atom to which they are attached, a heterocyclic ring which can include a second heteroatom such as oxygen, sulfur or nitrogen, the latter being optionally substituted by a lower alkyl or phenyl radical optionally substituted by one or more halogen atoms, a lower alkyl radical, or a lower alkoxy or trifluoromethyl radical; and in which X represents hydrogen, a halogen, lower alkyl, lower alkoxy, trifluoromethyl, nitro, cyano, carboxy or alkoxycarbonyl.

The invention also comprises addition salts of the compounds of formula I with pharmaceutically-acceptable inorganic and organic acids.

By lower alkyl or lower alkoxy is meant a $C_1$-$C_4$ saturated hydrocarbon chain.

By aralkyl is meant a benzyl or phenylethyl group.

By heteroalkyl or heteroaralkyl is meant a (3-pyridyl)methyl or (4-pyridyl)-methyl group.

The compounds of formula (I) above have at least two asymmetric center, and can exist in the form of several isomers (diastereoisomers and enantiomers). The invention relates to each isomer and to their mixtures.

Derivatives of thieno-pyridine have been described in French Pat. No. 2,215,948. Among them, Ticlopidine, otherwise know as 5-[(2-chlorophenyl) methyl]4,5,6,7-tetrahydrothieno [3,2-] pyridine, endowed with interesting platelet- and thrombotic- anti-aggregating properties, has been the subject of numerous studies (Haemostasis, Vol. 13 supplement 1, 1983).

The invention also relates to a process for the preparation of the compounds of formula (I), characterized in that the acids, esters or amides of the invention are prepared in which Y represents respectively a hydroxy group (—OH), an alkoxy group (—OR) or an amino group —NR₃R₄ as defined above, by condensation of 5,6,7,7a-tetrahydro 4H-thieno [3,2-c]2-pyridone of formula (II):

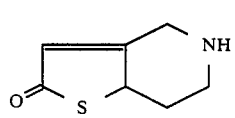

with an alpha-halogeno-phenyl acetic acid of the formula (IIIa):

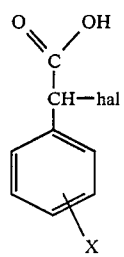

or with an alpha-halogeno-phenylacetate of the formula (IIIb):

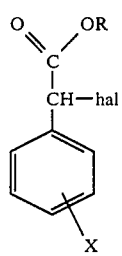

or with an alpha-halogeno-phenylacetamide of the formula (IIIc):

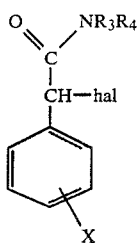

in which "hal" is a halogen, preferable selected from the group consisting of chlorine, iodine and bromine, and X, —OR and —NR$_3$R$_4$ take the definitions already given above, according to the reaction scheme:

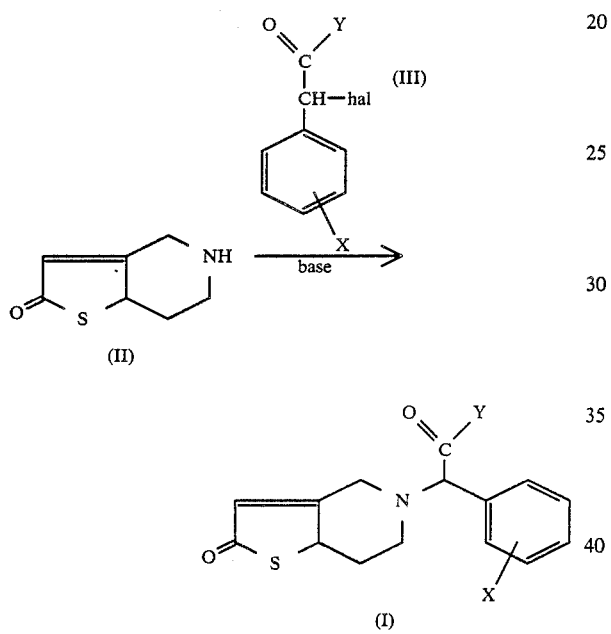

in which Y can be hydroxyl (—OH), alkoxy (—OR) or amino (—NR$_3$R$_4$).

This condensation reaction is carried out in the presence of a weak base, preferably a hydrogenated alkali metal carbonate such as sodium- or potassium-bicarbonate, in an inert solvent such as dimethylformamide, tetrahydrofuran or 1,2dimethoxyether, at a temperature between about 40° C. and the boiling point of the solvent.

The alpha-halogenated phenylacetic acids of formula (IIIa) and the alpha-halogenated esters of formula (IIIb) are prepared by known methods: (for example, E. L. Eliel, M. T. Fisk and T. Prosser, Organic Synthesis, Coll. Vol. IV, J. Wiley and Sons Inc., New York, 1963, p. 169).

The alpha-halogenated amides of formula (IIIc) are also prepared by known methods (for example, J. Malcolm Bruce and F. K. Sutcliffe, J. Chem. Soc., 1957, p. 4789).

The novel 5,6,7,7a-tetrahydro thieno-[3,2-c] 2-pyridone of formula (II) may be obtained by a process consisting of:

(a) fixing a triphenylmethyl (referred to hereinafter as trityl) protective group to the nitrogen function of 4,5,6,7-tetrahydro thieno [3,2-c] pyridine giving the compound of formula (IV):

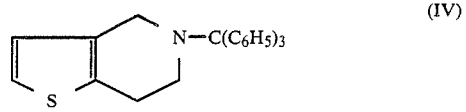

(b) next, fixing a boronic group—B(OR')$_2$ in position 2 to the thieno [3,2-c] pyridine skeleton, through the lithium derivative of formula (V) according to the reaction scheme:

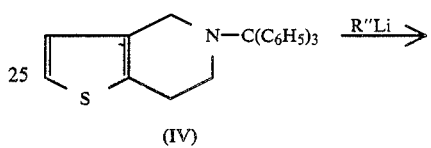

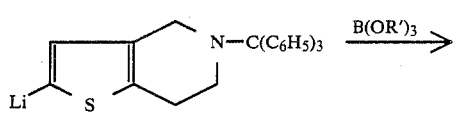

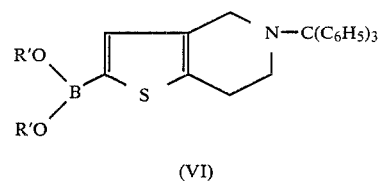

(c) next, oxidizing the boronic derivative of formula (VI) into the boric derivative of formula (VII):

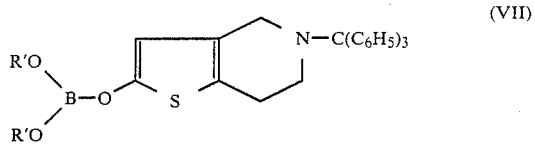

(d) next, immediately hydrolysing the compound of formula (VII) into the tritylated derivative of formula (VIII):

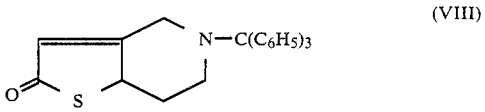

this compound being able to exist in the hydroxylated tautomeric form according to the tautomeric equilibrium:

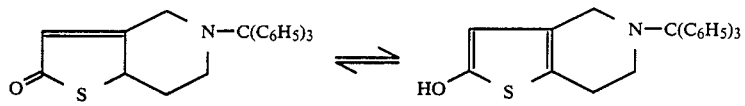

(e) next, selectively cleaving the trityl group by controlled acid hydrolysis, to obtain the 5,6,7,7a-tetrahydro 4H-thieno [3,2-c] 2-pyridone of formula (II).

The compound of formula (II) can also exist in the tautomeric hydroxylated form:

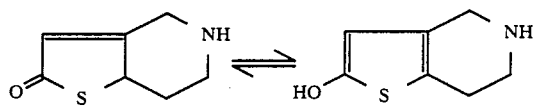

Steps (b), (c), and (d) are all carried out in the same reactor without isolation of the intermediates of formulae (V), (VI) and (VII).

More specifically, the tritylated derivative (IV) is prepared by condensation of triphenylmethyl chloride with 4,5,6,7-tetrahydro thieno [3,2-c] pyridine in the presence of an organic base serving as proton acceptor, preferably triethylamine, in an inert solvent such as dichloromethane, chloroform, tetrahydrofuran, 1,2-dimethoxyethane, or dimethylformamide. This condensation is preferably carried out at ambient temperature, e.g. 20° C.

The lithiation of the tritylated compound of formula (IV) with an alkyllithium R″Li compound such as butyllithium or a lithium amide such as lithium diisopropylamide leads to the lithiated derivative of formula (V). This metalation is effected preferably between 0° and 20° C. in an inert solvent such as hexane or tetrahydrofuran.

In the same reactor, this lithiated derivative (V) is condensed with an alkyl borate B(OR′)3 in which R′ is lower alkyl, preferably n-butyl, at a temperature between about −20° C. and −40° C., to yield the boron derivative of formula (VI).

In the same reactor, an aqueous 30% solution of hydrogen peroxide is added to oxidize the boron derivative of formula (VI) into the borate of formula (VII). The borate of formula VII is immediately hydrolyzed in the reaction medium, to give the tritylated derivative of formula (VIII).

The controlled acid hydrolysis of the tritylated derivative of formula (VIII) is carried out using, e.g., 98% formic acid, trifluoroacetic acid or a solution of hydrochloric acid gas in ethyl acetate at a concentration between about 2 and 5 moles per liter, at a temperature between about 40° C. and the reflux temperature of the reaction medium. This permits the selective splitting off of the trityl protective group, without cleavage of the thienopyridyl ring, resulting in the compound of formula (II).

In another embodiment, the esters and amides of formula (I) in which Y is an alkoxy group (—OR) or an amino group —NR$_3$R$_4$ and R, R$_3$ and R$_4$ are as defined above, are obtained from the acid of formula (I) in which Y is the hydroxyl group (—OH).

Although it is quite possible to obtain all of the esters of formula (I) in which Y is an alkoxy group (—OR) (R being as defined above) by reaction between compounds of formulae (II) and (IIIb), it is preferable, from an economic point of view, to prepare certain among them, particularly the higher esters, from the acid of formula (I) in which Y is hydroxyl (—OH), and the alcohol R—OH (R being as defined in formula I), in the presence of hydrochloric acid gas or of thionyl chloride, by known methods, according to the reaction scheme:

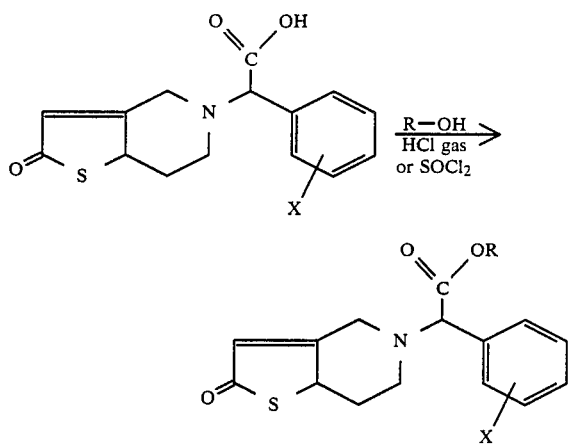

In another reaction scheme, the amides of formula (I) in which Y is an amino group —NR$_3$R$_4$ (R$_3$ and R$_4$ being as defined above) and certain of the esters of formula (I) in which Y is an alkoxy group (—OR) (R being as defined above) are prepared by the reaction of the acid of formula (I) in which Y is hydroxyl (—OH), with the appropriate amine HNR$_3$R$_4$ or with the appropriate alcohol (R—OH), preferably after activation of the acid.

The activation of the acid of formula (I) in which Y is hydroxyl (—OH) can be achieved by treatment with a lower alkyl chloroformate, preferably ethyl chloroformate or isobutyl chloroformate, in the presence of a slight excess of triethylamine, at a temperature between about −5° C. and −10° C., in an inert solvent such as chloroform, dichloromethane, 1,2-dimethoxy ethane or tetrahydrofuran. A mixed anhydride of formula (XI) is formed:

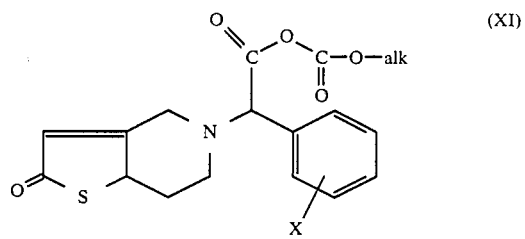

(alk can be, preferably, ethyl or isobutyl) whose treatment, in situ, by a slight excess of the amine HNR$_3$R$_4$, or alcohol (R—OH), at a temperature between about 10° C. and room temperature, yields the amide or ester of formula (I) according to the reaction scheme:

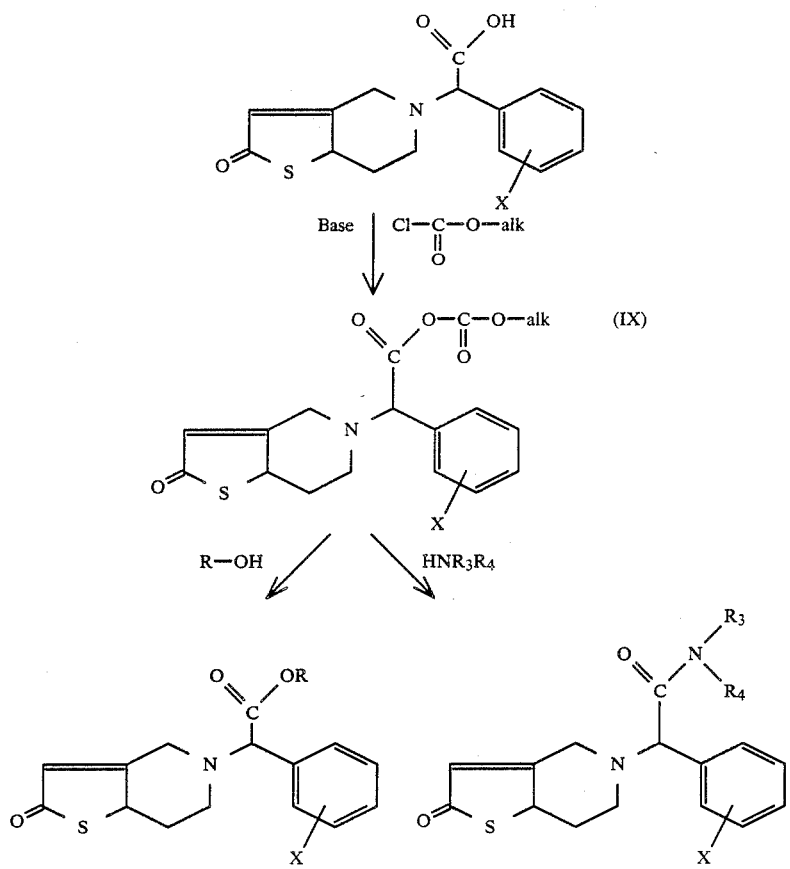

The activation of the acid of formula (I) in which Y is hydroxyl (—OH) can also be achieved in various other ways. For example, amides of formula (I) have also been prepared, in which Y is an amino group —NR₃R₄ (R₃ and R₄ being as defined above) by condensing the acid of formula (I) in which Y is hydroxy (—OH), with the amine HNR₃R₄, in the presence of dicyclohexylcarbodiimide in solution in 1,2-dichloroethane or in the presence of dicyclohexylcarbodiimide and of N-hydroxybenzotriazole in solution in dichloromethane.

According to another modification, the acid of formula (I) in which Y is hydroxyl (—OH) may be obtained by selective hydrolysis of an ester of formula (I) in which Y is an alkoxy group (—OR) (R being as defined above), according to the reaction scheme:

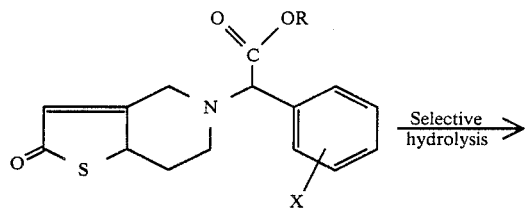

-continued

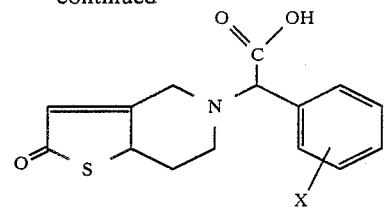

More particularly, the hydrolysis of the tert-butyl ester of formula (I) (R=tert-butyl) is carried out in an acid medium such as trifluoroacetic acid, or 98% formic acid, at a temperature between about 5° C. and the boiling point of the reaction medium.

The following non-limiting examples are given by way of illustration of the invention.

EXAMPLE 1

5-triphenylmethyl 4,5,6,7-tetrahydro thieno [3,2-c] pyridine (IV)

To a solution of 100 g (0.718 mole) of 4,5,6,7-tetrahydro thieno [3,2-c]pyridine in 200 ml of dichloromethane, are added 80 ml (0.789 mole) of triethylamine, then 200.2 g (0.718 mole) of triphenylmethylchloride is added, drop by drop, at ambient temperature. The reaction medium is left overnight at ambient temperature. The reaction medium is poured into 2000 ml of water. The organic phase is decanted, dried over sodium sulfate and evaporated to dryness. The residue is purified by filtration on a silica bed (elution with dichloromethane). The product is white crystals, M.P.=95° C.

(pasty); yield: 96%; NMR $^1$H (in ppm) (CDCl$_3$): 7.57–6.90 (m, 15H); 6.80 (c, J =6.5 Hz, 1H); 6.43 (d, J=6.5 Hz, 1H); 3.35 (s, 14), 3.00–2.33 (m, 4H).

EXAMPLE 2

5-triphenylmethyl 5,6,7,7a-tetrahydro 4H-thieno [3.2-c]2-pyridone (VIII)

To a solution of 27 g (0.0707 mole) of 5-triphenylmethyl-4,5,6,7-tetrahydro thieno [3,2-c] pyridine (IV) in 300 ml of tetrahydrofuran, are added drop by drop, at 0° C., 5.31 ml of butyl lithium (1.6M solution in hexane) (0.085 mole). The mixture is stirred for 15 minutes at ambient temperature and then cooled to −20° C. and there are added at this temperature, drop by drop, 23 ml (0.085 mole) of tri-n-butyl borate dissolved in 50 ml of tetrahydrofuran. The mixture is stirred for 1 hour at 10° C. After cooling of the reaction medium to −40° C., there are added drop by drop 20.1 ml (0.177 mole) of 30% (v/v) aqueous hydrogen peroxide. The mixture is allowed to come back to room temperature and stirred at this temperature for 1 hour. Water is added to the reaction medium and it is extracted with dichloromethane. The organic extraction phase is washed with water and dried over sodium sulfate. Evaporation of the solvent to dryness leaves a residue which is crystallized in diisopropyl ether. The product is beige crystals, M.P.=210° C. (dec.), yield: 64%; IR (KBr); $v_c$=O: 1675 cm$^{-1}$; NMR $^1$H (in ppm) (CDCl$_3$); 7.48–6.96 (m,15H); 6.02 (s,1H); 4.08 (m,1H); 3.78–1.43 (m,6H).

EXAMPLE 3

5,6,7,7a-tetrahydro 4H-thieno [3,2-c] 2-pyridone (II)

There are heated to 90° C., for 1 hour, 56.9 g (0.143 mole) of 5-triphenylmethyl 5,6,7,7a-tetrahydro 4H-thieno [3,2-c] 2-pyridone (VIII) in 350 ml of 98% formic acid. After cooling, an excess of a saturated solution of hydrochloric gas in diethyl ether is added and the reaction medium is concentrated to 100 ml. Then 1000 ml of diethyl ether are added and the crystals obtained filtered and washed with diethyl ether. The crystals obtained are redissolved in water and the aqueous solution, after treatment with animal black (bone black) and filtration on a celite bed, is freeze-dried. The crystals so obtained are washed successively with acetone and then with diethyl ether and dried. The product is cream-colored crystals, M.P.=210° C. (dec.), yield: 81%; NMR $^1$H in ppm (DMSO-d$_6$): 6:47 (s.1H); 4.97–4.58 (m,1H); 4.46–3.83 (2d,2H).

EXAMPLE 4

Methyl alpha - (2-oxo 2,4,5,6,7,7a-hexahydro thieno [3.2-c] 5-pyridyl)(2-chloro phenyl)-acetate (in formula I: Y=(—OCH$_3$); X=2-Cl); (Derivative no. 1)

To a solution of 10 g (0.052 mole) of 5,6,7,7a-tetrahydro 4H-thieno [3,2-c] 2-pyridone hydrochloride (II) in 100 ml of dimethylformamide, are added 10.43 g (0.104 mole) of potassium bicarbonate and 7.82 g (0.052 mole) of sodium iodide, then 11.65 g (0.0532 mole) of methyl alpha-chloro (2-chloro phenyl)-acetate (in formula IIIb: R=CH$_3$; X=2-Cl; hal=Cl). The reaction medium is heated to 60° C. for 90 minutes. After cooling, the reaction medium is poured into 600 ml of water. It is extracted with ethyl acetate, and the organic extract is washed with water. The organic phase is dried over sodium sulfate. Evaporation of the solvent leaves a residue which is purified by filtration on a silica bed (elution with ethyl acetate). The oily product obtained is converted into the hydrochloride, for eventual purification. The product hydrochloride is white crystals, M.P.=130° C. (dec.), yield: 58%; IR (KBr); $v_c$=O (ester): 1745 cm$^{-1}$; $v_c$=O (thiolactone): 1680 cm$^{-1}$; NMR $^1$H in ppm (DMSO-d$_6$): 7.43 (m, 4H); 6.27 (s,1H); 5.33 and 5.25 (s,1H, 2 diastereoisomers); 4.77–4.38 (m,1H); 3.67 (s,3H).

EXAMPLE 5

Methyl alpha (2-oxo 2,4,5,6,7,7a-hexahydro thieno [3,2-c] 5-pyridyl) phenyl-acetate (in formula I: Y=—OCH$_3$; X=H) (Derivative no. 2)

This compound is prepared by the operational method described in Example 4 by alkylation of 5,6,7,7a-tetrahydro 4H-thieno [3,2-c] 2-pyridone (II) with methyl alphachlorophenylacetate (in formula IIIb: R=—CH$_3$; X=H; hal=Cl). The product in hydrobromide form is white crystals, M.P.=205° C. (dec.), yield 86%; IR (KBr): $v_c$=o (ester): 1745 cm$^{-1}$; $v_c$=O (thiolactone): 1695 cm$^{-1}$; NMR $^1$H in ppm (DMSO-d$_6$): 7.60 (m,5H); 6.57 (s,1H); 5.83 (s,1H); 3.77 (s,3H).

EXAMPLE 6

Methyl alpha-(2-oxo 2,4,5,6,7,7a-hexahydro thieno [3,2-c] 5-pyridyl) (2-fluoro phenyl)-acetate (in formula I: Y=—OCH$_3$; X=2-F) (Derivative no. 3)

This compound is prepared by the operational method described in Example 4 by alkylation of 5,6,7,7a-tetrahydro 4H-thieno [3,2-c] 2-pyridone (II) with methyl alpha-chloro (2-fluoro phenyl)-acetate (in formula IIIb: R=—CH$_3$; X=2-F; hal=Cl). The product in hydrobromide form is white crystals, M.P.=213° C., yield: 70%; IR (KBr): $v_c$=O (ester): 1745 cm$^{-1}$; $v_c$=O (thiolactone): 1690 cm$^{-1}$; NMR $^1$H in ppm (DMSO-d$_6$): 7.48 (m,4H); 6.43 (s,1H); 5.60 (s,1H) 4.83–3.87 (m,3H); 3.72 (s,3H).

EXAMPLE 7

Ethyl alpha-(2-oxo 2,4,5,6,7,7a-hexahydro thieno [3,2-c] 5-pyridyl)(2-chloro phenyl)-acetate (in formula I: Y=—OC$_2$H$_5$; X=2-Cl) (Derivative no. 4)

This compound is prepared by the operational method described in Example 4 by alkylation of 5,6,7,7a-tetrahydro 4H thieno [3,2-c] 2-pyridone (II) with ethyl alpha-chloro (2-chloro phenyl)-acetate (in formula IIIb: R=C$_2$H$_5$; X=2-Cl; hal =Cl). The product in hydrobromide form is white crystals, M.P. 200° C., yield: 64%; IR (KBr): $v_c$=O (ester): 1755 cm$^{-1}$; $v_c$=O (thiolactone): 1690 cm$^{-1}$; NMR $^1$H in ppm (DMSO-d$_6$): 7.52 (m,4H); 6.53 (s,1H); 5.78 (s,1H); 4.30 (m,2H), 1.18 (t,J=7Hz, 3H).

EXAMPLE 8

Ethyl alpha-(2-oxo 2,4,5,6,7,7a-hexahydro thieno [3,2-c] 5-pyridyl) 2-methyl phenyl)-acetate (in formula I: Y=—OC$_2$H$_5$; X=2—CH$_3$) (Derivative no. 5)

This compound is prepared by the operational method described in Example 4 by alkylation of 5,6,7,7a-tetrahydro 4H-thieno [3,2-c] 2-pyridone (II) with ethyl alpha-chloro (2-methyl phenyl)-acetate (in formula IIIb: R=C$_2$H$_5$; X=2-CH$_3$; hal=Cl). The product in hydrobromide form is white crystals, M.P.=222° C. (dec.), yield: 79%; IR (KBr): $v_c$=O (ester: 1748 cm$^{-1}$; $v_c$=O (thiolactone): 1685 cm$^{-1}$; NMR $^1$H in ppm (DMSO-d6): 7.38 (m,4H); 6.60 (s,1H); 5.60 (s,1H); 4.23 (m,2H); 2.53 (s,3H); 1.13 (t,J=7Hz. 3H).

EXAMPLE 9

Isopropyl alpha-(2-oxo 2,4,5,6,7,7a-hexahydro thieno [3,2-c] 5-pyridyl)(2-chloro phenyl)-acetate (in formula I: Y=—OCH—(CH$_3$)$_2$; X=2-Cl) (Derivative no. 6)

This compound is prepared by the operational method described in Example 4 by alkylation of 5,6,7,7a-tetrahydro 4H-thieno [3,2-c] 2-pyridone (II) with isopropyl alpha-chloro (2-chloro phenyl)-acetate (in formula IIIb: R=—CH(CH$_3$)$_2$; X=2-Cl; hal=Cl). The product in hemisulfate form is beige crystals, M.P.=110° C., yield: 69%; IR (KBr): $v_c$=O (ester): 1750 cm$^{-1}$; $v_c$=O (thiolactone): 1690 cm$^{-1}$; NMR $^1$H in ppm (DMSO-d6): 7.50 (m,4H); 6.36 and 6.28 (s,1H.2 diastereoisomers 5.36 and 5.28 (s,1H,2 diastereoisomers, 1.33–0.87 (m,6H).

EXAMPLE 10

Tert-butyl alpha-(2-oxo 2,4,5,6,7,7a-hexahydro thieno [3,2-c] 5-pyridyl) (2-chloro phenyl)-acetate (in formula I: Y=—OC(CH$_3$)$_3$; X=2-Cl) (Derivative no. 7)

This compound is prepared by the operational method described in Example 4 by alkylation of 5,6,7,7a-tetrahydro 4H thieno [3,2-c] 2-pyridone (II) with tert-butyl alpha-chloro (2-chloro phenyl) acetate (in formula IIIb: R=C(CH$_3$)$_3$; X=2-Cl; hal=Cl). The product is obtained as a base, oil: yield, 69%; IR (film): $v_c$=O (ester): 1740 cm$^{-1}$; $v_c$=O (thiolactone): 69PO cm$^{-1}$; NMR $^1$H in ppm (DMSO-d6); 7.36 (m,4H); 6.02 (s,1H); 4.63 (s,1H); 4.76–4.13 (m,1H); 1.40 (m,9H).

EXAMPLE 11

N-[alpha-(2-oxo 2,4,5,6,7 a-hexahydro thieno [3,2-c]-5-pyridyl) (2-chloro phenyl)]-acetyl pyrrolidine (in formula I:

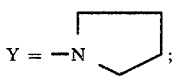

X=2-Cl) (Derivative no. 8)

To a solution of 4.5 g (0.023 mole) of 5,6,7,7a-tetrahydro 4H-thieno [3,2-c] 2-pyridone hydrochloride (II) in 45 ml of dimethylformamide, are added 4.7 g (0.047 mole) of potassium bicarbonate and then 3.5 g of sodium iodide. To this reaction medium are added 6.1 g (0.023 mole) of alpha-chloro (2-chloro phenyl)-acetyl pyrrolidine (in formula IIIc:

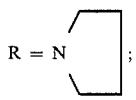

X=2-Cl; hal=Cl) and the whole of the reagents are maintained at 60° C. for two hours. After cooling, ethyl acetate is added. The organic solution is washed with water, then dried over sodium sulfate. It is evaporated to dryness and the residue is purified by filtration on a silica bed (eluant: ethyl acetate). The subsequent purification is done by conversion into the hydrochloride in ethyl ether. The product in hydrochloride form is white crystals, M.P.=150° C., yield: 69%; IR (KBr): $v_c$=O (thiolactone): 1690 cm$^{-1}$; $v_c$=O (amide): 1650 cm$^{-1}$; NMR $^1$H in ppm (CDCl$_3$): 7.31 (m,4H); 5.90 (s,1H); 4.90 (s,1H).

EXAMPLE 12

N,N-dimethyl alpha-(2-oxo 2,4,5,6,7,7a-hexahydro thieno [3,2-c] 5-pyridyl) (2-chloro phenyl)-acetamide (Derivative no. 9)

This compound is prepared by the operational method described in Example 11 by alkylation of 5,6,7,7a-tetrahydro 4H thieno [3,2-c] 2-pyridone (II) with N,N-dimethyl alpha-chloro (2-chloro phenyl)-acetamide (in formula IIIc: R$_3$ and R$_4$ are —CH$_3$; X=2-Cl; hal=Cl). The product in hydrochloride form is white crystals, M.P.=145° C., yield: 75%. IR (KBr): $v_c$=O (thiolactone): 1690 cm$^{-1}$; $v_c$=O (amide): 1655 cm$^{-1}$; NMR $^1$H in ppm (DMSO-d6): 7.70 (m,4H); 6.08 and 6.00 s,1H,2 diastereoisomers) 2.93 (s,6H).

EXAMPLE 13

Alpha-(2-oxo 2,4,5,6,7,7a-hexahydro thieno 3,2-c] 5-pyridyl)(2-chloro phenyl)-acetic acid (in formula I: Y=OH; X=2-Cl) (Derivative no. 10)

(a) Direct alkylation of 5,6,7,7a-tetrahydro 4H-thieno [3,2-c] 2-pyridone (II)

To a solution of 1 g (0.00522 mole) of 5,6,7,7a-tetrahydro 4H-thieno [3,2-c] 2-pyridone (II) in 15 ml of dry dimethylformamide, are added 1.09 g (0.011 mole) of potassium bicarbonate and 0.8 g (0.0052 mole) of sodium iodide, then 1.07 g (0.00522 mole) of alpha-chloro (2-chloro phenyl)-acetic acid (in formula IIIa: X=2-Cl; hal=Cl) and it is maintained at 60° C. for 2½ hours. The reaction medium is poured into an excess of 1N hydrochloric acid. The precipitate is filtered, washed with water, then washed with acetone and diethyl ether. The beige crystals obtained are dried in the oven. Yield: 60%

(b) Selective hydrolysis of the ester

A solution of 9 g (0.024 mole) of tert-butyl alpha-(2-oxo 2,4,5,6,7,7a-hexahydro thieno [3,2-c] 5-pyridyl (2-chloro phenyl)-acetate (in formula I: Y=OC(CH$_3$)$_3$; X=2-Cl) in 50 ml of trifluoroacetic acid are stirred at ambient temperature overnight. It is evaporated to dryness and the residue crystallized in diisopropyl ether. The beige crystals obtained (M.P.=about 100° C., pasty melting) are dissolved in 100 ml of 2N hydrochloric acid. There is dissolution and then reprecipitation. The crystals are drained, washed with water and dried. The product is beige crystals, M.P.=210° C., yield: 80%; IR (KBr): $v_c$=O (acid): 1725 cm$^{-1}$; $v_c$=O (thiolactone): 1690 cm$^{-1}$; NMR $^1$H in ppm (CF$_3$ COOD): 7.52 (m,4H); 6.53 (s,1H); 5.80 (s,1H).

EXAMPLE 14

2-phenyl ethyl alpha-(2-oxo 2,4,5,6,7,7a-hexahydro thieno [3,2-c] 5-pyridyl) (2-chloro phenyl)-acetate (in formula I: Y=OCH$_2$ CH$_2$C$_6$H$_5$; X=2-Cl)

This compound is prepared by the operational method described in Example 4 by alkylation of 5,6,7,7a-tetrahydro 4H-thieno [3,2-c] 2-pyridone (II) with 2-phenyl ethyl alpha-chloro (2-chloro phenyl) acetate (in formula IIIb: R=CH$_2$CH$_2$C$_6$H$_5$; X=2-Cl; hal=Cl). The product in hydrochloride form is beige crystals, M.P.=175° C. (acetone); yield: 71%; IR (KBr): $v_c=O$ (ester): 1755 cm$^{-1}$; $v_c=O$ (thiolactone): 1690 cm$^{-1}$; NMR $^1$H in ppm (DMSO-d6); 7.80–6.83 (m,9H,aromatics); 6.28 (s,1H) 5.46 and 5.28 (s,1H,2 diastereoisomers).

EXAMPLE 15

N-[Alpha-(2-oxo 2,4,5,6,7,7a-hexahydro thieno 3,2-c] 5-pyridyl (2-chloro phenyl)]-acetyl morpholine (In formula I:

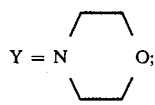

X=2-Cl)

This compound is prepared by the operational method described in Example 11 by alkylation of 5,6,7,7a-tetrahydro 4H-thieno [3,2-c] 2-pyridone (II) with alpha-chloro (2-chloro phenyl)-acetYl morpholine (in formula IIIc: R$_3$ and R$_4$ together form

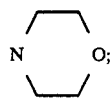

X=2-Cl; hal=Cl). The product in hydrochloride hydrate form is white crystals, M.P.=150° C.; yield: 60%; IR (KBr): $v_c=O$ (thiolactone): 1690 cm$^{-1}$; $v_c=O$ (amide): 1660 cm$^{-1}$; NMR $^1$H in ppm (DMSO-d6): 7.51 (m,4H); 6.45 and 6.26 (s, 1H, 2 diastereoisomers); 4.88 and 4.73 (s, 1H, 2 diastereoisomers).

EXAMPLE 16

N-(3-pyridyl methyl) alpha-(2-oxo-2,4,5,6,7,7a-hexahydro thieno [3,2-c] 5-pyridyl(2-chloro phenyl)-acetamide (In formula I:

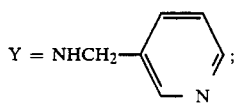

X=2-Cl)

This compound is prepared by the operational method described in Example 11 by alkylation of 5,6,7,7a-tetrahydro 4H-thieno [3,2-c] 2-pyridone (II) with N-(3-pyridyl methyl)alphachloro(2-chloro phenyl)-acetamide (in formula IIIc: R$_3$=H, and

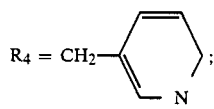

X=2-Cl; hal=Cl). The product in hydrochloride hydrate form is beige crystals, M.P.=165° C.; yield: 55%; IR (KBr): $v_c=O$ (thiolactone): 1690 cm$^{-1}$; $v_c=O$ (amide): 1660 cm$^{-1}$; NMR $^1$H in ppm (DMSO-d6); 5.52 and 5.43 (s, 1H, diastereoisomers).

EXAMPLE 17

Ethyl alpha-(2-oxo 2,4,5,6,7,7a hexahydro thieno 3,2-c] 5-pyridyl)(4-methoxy phenyl)-acetate (in formula I: Y=OC$_2$H$_5$; X=4—OCH$_3$)

This compound is prepared by the operational method described in Example 4 by alkylation of 5,6,7,7a-tetrahydro 4H-thieno [3,2-c] 2-pyridone (II) with ethyl alpha-chloro (4-methoxy phenyl)-acetate (in formula IIIb: R=C$_2$H$_5$; X=4—OCH$_3$; hal=Cl). The product in hydrochloride form is white crystals, M.P.=140° C.; yield: 91%; IR (KBr): $v_c=O$ (ester): 1715 cm$^{-1}$; $v_c=O$ (thiolactone): 1690 cm$^{-1}$; NMR $^1$H in ppm (DMSO-d6): 7.65 (m, 4H); 6.53 and 6.61 (s, 1H, 2 diastereoisomers); 5.73 and 5.63 (s, 1H, 2 diastereoisomers); 3.80 (s,3H).

EXAMPLE 18

[2-(N,N-diethyamino) ethyl alpha-(2-oxo 2,4,5,6,7,7a-hexahydro thieno [3,2-c] 5-pyridyl)(2-chloro phenyl)acetate (in formula I: Y =OCH2CH2N(C2H5)$_2$; X =2-Cl)

This compound is prepared by the operational method described in Example 4 by alkylation of 5,6,7,7a-tetrahydro 4H-thieno [3,2-c] 2-pyridone (II) with 2- N,N-diethylamino alphachloro (2-chloro phenyl)-acetate (in formula IIIb: R=CH$_2$CH$_2$N(C$_2$H$_5$)$_2$; X=2-Cl; hal=Cl). The product in oxalate form is beige crystals, M.P.=130° C.; yield: 61%; IR (KBr): $v_c=O$ (ester): 1745 cm$^{-1}$; $v_c=O$ (thiolactone): 1685 cm$^{-1}$; NMR $^1$H in ppm (DMSO-d6): 7.64–7.25 (m, 4H); 6.23 (s, 1H); 4.94 (s, 1H).

EXAMPLE 19

Alpha-(2-oxo 2,4,5,6,7,7a-hexahydro thieno [3.2-c] 5-pyridyl)(2-chloro phenyl)-acetamide (in formula I: Y=NH$_2$; X=2-Cl)

This compound is prepared by the operational method described in Example 11 by alkylation of 5,6,7,7a-tetrahydro 4H-thieno [3,2-c] 2-pyridone (II) with alpha-chloro (2-chloro phenyl)-acetamide (in formula IIIc: R$_3$, R$_4$=H; X=2-Cl; hal=Cl). The product in hydrochloride form is beige crystals, M.P.=185° C., yield: 53%; IR (KBr): $v_c=O$ (thiolactone): 1685 cm$^{-1}$; $v_c=O$ (amide): 1640 cm$^{-1}$.

PHARMACOLOGY AND TOXICOLOGY

The pharmacological and toxicological results which are reported below demonstrate the properties of the derivatives of th invention both from the point of view of toxicity and tolerance, and from the point of view of their activities, particularly inhibition of platelet and thrombotic aggregation.

The invention therefore also relates to a medicament having in particular, inhibiting activities of platelet and thrombotic aggregation, characterized in that it contains, as active principle, a derivative of formula (I) or an addition salt thereof with a pharmaceutically-acceptable inorganic or organic acid.

TOXICOLOGICAL STUDY

The compounds of the invention demonstrate excellent tolerance and low toxicity.

In addition, the tests carried out on the acute, chronic, subchronic and delayed toxicities in different species of animals, have not demonstrated any local or general reaction, disturbance or anomaly in the biochemical, macroscopic or microscopic examinations carried out during these experiments.

PHARMACOLOGICAL STUDY

This study, which was carried out as a comparison with the most representative compound of the above-mentioned French Pat. No. 2,215,948, Ticlopidine, has demonstrated the platelet and thrombotic aggregation-inhibiting actions of the derivatives of the invention.

(1) Inhibiting action on platelet aggregation

These experiments were carried out on a rat which received, orally, X mg of the compounds of the invention at the time −2 hours. At the time 0 hours, 4 ml of blood were taken up by the Renaud technique, at the jugular vein of the anesthetized animal. It is the citrated blood which is used in the aggregation measurements.

(a) measurement of platelet aggregation with A.D.P.

2 ml of citrated blood are rapidly poured into a small beaker placed on a magnetic stirrer and provided with a magnetic rod. After several seconds of stirring there are introduced into the beaker 0.4 ml of a solution containing 0.66 g of adenosinediphosphate (A.D.P.) per ml. After 90 seconds stirring, two blood samplings of 0.5 ml were made:
- the first is mixed with 0.5 ml of an EDTA-Formol solution,
- the second is mixed with 0.5 ml of an EDTA solution alone.

The EDTA-Formol addition is for the purpose of stabilizing the blood and hence of fixing the aggregation while the EDTA causes, on the contrary, deaggregation of all the platelet aggregates.

After standing for 10 minutes and centrifugation of the two mixtures at slow speed for 5 minutes, in order to separate the red blood cells, the platelet-rich plasma (PRP) supernatant liquor is taken off, diluted and counted in platelets.

The intensity of aggregation is determined by the ratio $$\frac{\text{number of platelets in EDTA-Formol}}{\text{number of platelets in EDTA}} \times 100 =$$

percentage of non aggregated platelets

The product under test is proportionately more platelet-aggregation-inhibiting as the ratio approaches 100.

(b) measurement of platelet aggregation with collagen 1.5 ml of citrated blood is supplemented with 0.10 ml of a solution containing 10 g of collagen per ml. While the medium is kept under stirring, the counting of the platelets is carried out without interruption.

The reduction in the number of free platelets as a function of time is followed continuously and enables a graph to be traced whose slope gives the initial aggregation speed.

The most significant results are collected in the table below.

(2) Antithrombotic activity

This activity was studied by the spiral venous thrombosis method.

It consists of an adaptation of the method of Friedman and Coll (AM. J. PHYSIOL., 1960, 199, 770–774). A recut metal spiral (dental paste-ram) is inserted in the inferior vena cava of a rat which received, 2 hours previously, oral treatment with the compound being tested, in suspension in 10 ml/kg of a 5% aqueous gum arabic solution.

Five hours later, this spiral is taken out with the thrombus that it retains, dried carefully by successive dabbing on filter paper and weighed. The spiral is then freed from the thrombus, dried and weighed again. In this way by difference, the mean weight of the thrombus is obtained.

The most significant results are collected in the table below.

| Compounds | Oral doses in mg/kg | % non-aggregated platelets | % inhibition | Significance (p) |
|---|---|---|---|---|
| ANTI-AGGREGATING ACTIVITY WITH RESPECT TO ADP | | | | |
| Control Derivative no. 1 | 2.5 | 5 ± 1 54 ± 12 | 52 | 0.001 |
| Control Derivative no. 1 | 5.0 | 6 ± 1 96 ± 2 | 95 | 0.001 |
| Control Derivative no. 2 | 5.0 | 3 ± 0 47 ± 12 | 45 | 0.05 |
| Control Derivative no. 3 | 5.0 | 3 ± 0 83 ± 2 | 82 | 0.001 |
| Control Derivative no. 4 | 5.0 | 5 ± 1 49 ± 18 | 46 | 0.05 |
| Control Derivative no. 5 | 5.0 | 5 ± 1 70 ± 17 | 68 | 0.05 |
| Control Ticlopidine | 300.0 | 8 ± 1 10 ± 1 | 2 | ns |
| Control Ticlopidine | 100.0 × 3 days | 16 ± 4 60 ± 7 | 52 | 0.001 |

| Compounds | Oral doses in mg/kg | Aggregation slope | % inhibition | Significance (p) |
|---|---|---|---|---|
| ANTI-AGGREGATING ACTIVITY WITH RESPECT TO COLLAGEN | | | | |
| Control Derivative no. 1 | 2.5 | 1.18 ± 0.11 0.11 ± 0.03 | 91 | 0.001 |
| Control Derivative no. 1 | 5.0 | 2.48 ± 0.32 0 | 100 | 0.001 |
| Control Derivative no. 2 | 5.0 | 1.71 ± 0.52 0.15 ± 0.10 | 91 | 0.01 |
| Control Derivative no. 3 | 5.0 | 1.71 ± 0.52 0.06 ± 0.04 | 95 | 0.01 |
| Control Derivative no. 4 | 5.0 | 1.94 ± 0.16 0.65 ± 0.24 | 66 | 0.01 |
| Control Ticlopidine | 300.0 | 10.3 ± 1.17 7.94 ± 1.33 | 23 | ns |
| Control Ticlopidine | 100.0 × 3 days | 5.1 ± 0.2 2.2 ± 0.2 | 58 | 0.01 |

| Compounds | Oral doses in mg/kg | Weight of Thrombus in mg | % inhibition | Significance (p) |
|---|---|---|---|---|
| ANTITHROMBOTIC ACTIVITY IN THE MODEL OF THE SPIRAL | | | | |
| Control Derivative no. 1 | 12.5 | 3.44 ± 0.35 1.49 ± 0.18 | 57 | 0.021 |

-continued

ANTITHROMBOTIC ACTIVITY IN THE MODEL OF THE SPIRAL

| Compounds | Oral doses in mg/kg | Weight of Thrombus in mg | % inhibition | Significance (p) |
|---|---|---|---|---|
| Control Derivative no. 1 | 25.0 | 4.82 ± 0.31 1.18 ± 0.18 | 76 | 0.001 |
| Control Derivative no. 2 | 25.0 | 5.03 ± 0.59 1.69 ± 0.16 | 66 | 0.001 |
| Control Derivative no. 3 | 25.0 | 3.28 ± 0.29 0.94 ± 0.05 | 72 | 0.001 |
| Control Derivative no. 4 | 25.0 | 5.25 ± 1.79 1.63 ± 0.08 | 69 | 0.001 |
| Control Derivative no. 5 | 25.0 | 3.90 ±.0.40 1.65 ± 0.14 | 58 | 0.001 |
| Control Derivative no. 6 | 25.00 | 3.90 ± 0.40 2.63 ± 0.20 | 33 | 0.01 |
| Control Ticlopidine | 200.0 | 5.52 ± 0.37 5.05 ± 0.48 | 8 | ns |
| Control Ticlopidine | 200.0 × 3 days | 4.47 ± 2.03 2.03 ± 0.25 | 54 | 0.001 |

The toxicological and pharmacological studies reported directly above demonstrate the low toxicity of the compounds of the invention, as well as their excellent tolerance and their interesting platelet- and thrombotic-aggregation-inhibiting properties which render them very useful in human and veterinary therapeutics.

The medicaments of the invention may be presented for oral administration in the form of tablets, dragees, capsules, drops, granulates or syrup. They can also be presented for rectal administration in the form of suppositories, and for parenteral administration in the form of an injectable solution.

Each unit dose contains, advantageously from 0.005 g to 0.25 g of a derivative of the invention, and the doses administrable daily can vary from 0.005 g to 1.00 g of active principle according to the age of the patient and of the severity of the disease treated.

Below will be given, by way of non-limiting examples, some pharmaceutical formulations of the medicaments of the invention.

(1) Tablets
Derivative No. 1   0.100 g
Excipient:   corn starch, lactose, dicalcium phosphate, magnesium stearate (2) Dragees
Derivative No. 2   0.100 g
Excipient:   levilite, potato starch, stearic acid, gum lac, talc, powdered gum arabic, crystalline sugar, carnauba wax, orange yellow S.

(3) Capsules
Derivative No. 5   0.100 g
Excipient:   magnesium stearate, levilite, corn starch, lactose.

(4) Injectable solution
Derivative No. 9   0.075 g
Isotonic solvent q.s.p.   5 ml (5) Suppositories
Derivative No. 10   0.100 g
Semi-synthetic triglycerides q.s.p.   1 suppository By their inhibiting properties of platelet and thrombotic aggregation, the medicaments of the invention are indicated in the prevention and treatment of disorders causing pathological modification of platelet aggregation, such as thrombo-embolic disorders.

We claim:

1. A compound of the formula

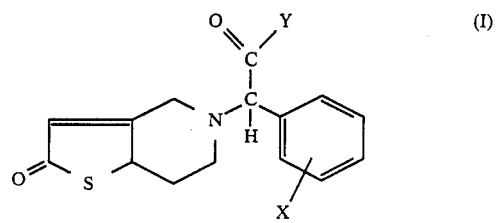

in which Y represents hydroxyl (—OH): or Y represents (—OR) in which R is a linear or branched $C_1$-$C_4$ alkyl radical or a benzyl or phenylethyl radical, or a phenyl- substituted benzyl of phenylethyl radical, or a dialkyl amino group of the formula:

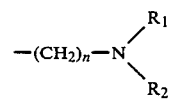

in which n represents a whole number from 0 to 4, $R_1$ and $R_2$ are each a $C_1$-$C_4$ alkyl radical or Y represents an amino group of the formula

in which $R_3$ and $R_4$ may be the same or different and are each hydrogen or a linear or branched $C_1$-$C_4$ alkyl group, a phenyl, benzyl, phenylthyl, substituted benzyl or substituted phenylethyl group, a (3-pyridyl) methyl or (4-pyridyl) methyl group, or $R_3$ and $R_4$ from together with the nitrogn atom to which they are attached, a pyrrolidiono or morpholino group, these being unsubstituted or substituted by $C_1$-$C_4$ alkyl radical, a phenyl radical, or a phenyl radical substituted by at least one member of the group consisting of halogen, $C_1$-$C_4$ alkyl, $C_1$-$C_4$ alkoxy, or trifluoromethyl; where X represent hydrogen, halogen, $C_1$-$C_4$ alkyl, $C_1$-$C_4$ alkoxy, trifluoromethyl, nitro, cyano, carboxy or a $C_1$-$C_4$ alkoxy carbonyl; and the acid addition salts with pharmaceutically acceptable inorganic and organic acids.

2. An addition salt of a compound of claim 1 with a pharmaceutically-acceptable inorganic or organic acid.

3. A mixture of at least two isomers of a compound of claim 1.

4. Methyl alpha-(2-oxo 2,4,5,6,7,7a-hexahydro thieno [3,2-c] 5-pyridyl) (2-chloro phenyl)-acetate.

5. Methyl alpha-(2-oxo 2,4,5,6,7,7a-hexahydro thieno [3,2-c] 5-pyridyl) phenyl-acetate.

6. Methyl alpha-(2-oxo 2,4,5,6,7,7a-hexahydro thieno [3,2-c] 5-pyridyl) (2-fluoro phenyl)-acetate.

7. Ethyl alpha-(2-oxo 2,4,5,6,7,7a-hexahydro thieno [3,2-c] 5-pyridyl) (2-chloro phenyl)-acetate.

8. Ethyl alpha-(2-oxo 2,4,5,6,7,7a-hexahydro thieno [3,2-c] 5-pyridyl) (2-methyl phenyl)-acetate.

9. Isopropyl alpha-(2-oxo 2,4,5,6,7,7a-hexahydro thieno [3,2-c] 5-pyridyl) (2-chloro phenyl)-acetate.

10. Tert-butyl alpha-(2-oxo 2,4,5,6,7,7a-hexahydro thieno [3,2-c] 5-pyridyl (2-chloro phenyl)-acetate.

11. N alpha-(2-oxo 2,4,5,6,7,7a-hexahydro thieno [3,2-c] 5-pyridyl) (2-chloro phenyl)-acetyl pyrrolidine.

12. N,N-dimethyl alpha-(2-oxo 2,4,5,6,7,7a-hexahydro thieno [3,2-c] 5-pyridyl) (2-chloro phenyl)-acetamide.

13. Alpha-(2-oxo 2,4,5,6,7,7a-hexahydro thieno [3,2-c]5-pyridyl) (2-chloro phenyl)-acetic acid.

14. A platelet- and thromboticaggregation-inhibition composition, comprising as the active ingredient, in an amount effective thereof, a compound according to formula (I), or an acid addition salt of a compound according to formula (I) with a pharmaceutically-acceptable inorganic or organic acid, or a mixture of two or more isomers according to formula (I), together with a pharmaceutically acceptable carrier.

15. The composition according to claim 14, in a dosage form suitable for oral, parenteral or rectal administration.

16. The composition according to claim 14 or 15, in the form of a unit dose containing 0.005 g to 0.250 g of the active ingredient.

* * * * *